US00PP10292P

United States Patent [19]

Zaiger et al.

[11] Patent Number: Plant 10,292

[45] Date of Patent: Mar. 24, 1998

[54] INTERSPECIFIC TREE "HONEY RICH"

[76] Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, Calif. 95358

[21] Appl. No.: 794,453

[22] Filed: Feb. 4, 1997

[51] Int. Cl.[6] ..... A01H 5/00

[52] U.S. Cl. ..... Plt./39

[58] Field of Search ..... Plt./38, 38.1, 39

*Primary Examiner*—James R. Feyrer

[57] ABSTRACT

A new and distinct variety of Interspecific [(*Prunus armeniaca*×(*Prunus salicina*×*Prunus armeniaca*))×*Prunus salicina*]×*Prunus armeniaca*; its novelty consisting of the following combination of desirable features:

1. Regular and heavy production of early maturing fruit.
2. Fruit with very good flavor and eating quality.
3. Fruit with firm flesh, good handling and shipping quality.
4. Relatively uniform fruit size throughout the tree.
5. Fruit with a high degree of attractive orange skin color.
6. Vigorous, semi-spreading growth habit.

1 Drawing Sheet

ORIGIN OF THE VARIETY

The present new and distinctive variety of interspecific tree was originated by us in our experimental orchard located near Modesto, Calif., as a first generation cross between a selected seedling with field identification number 7HC43 and Tom Cot Apricot (U.S. Plant Pat. No. 7,034). The maternal parent (7HC43) originated from a cross between the selected seedling 87EB90 (apricot×plum cot) with Royal Zee Plum (U.S. Plant. Pat. No. 5,486). The selection (87EB90) originated from an open pollinated Flaming Gold Apricot (U.S. Plant Pat. No. 2,822) seedling crossed with a plum-cot seedling which originated from an open pollinated Red Beaut Plum (U.S. Plant Pat. No. 2,539) seed. We grew and maintained a large group of these first generation seedlings under close and careful observation. The present variety evidenced distinctive desirable fruit characteristics and was selected for asexual reproduction and commercialization.

ASEXUAL REPRODUCTION OF THE VARIETY

Asexual reproduction of the new and distinct variety of interspecific tree was by budding, as performed by us in our experimental orchard located near Modesto, Calif., and shows that all characteristics of the tree and its fruit run true to the original tree and are established and transmitted through succeeding asexual propagations.

SUMMARY OF THE VARIETY

The new and distinct variety of interspecific tree is of large size, vigorous, semi-spreading growth; and is a regular and productive bearer of medium size, orange flesh, free-stone fruit with very good flavor and eating quality. The fruit shape and skin appearance are characteristic of an apricot with a high orange skin color. The flesh characterisitics resemble an apricot, except the flesh is firmer and meatier in texture and holds the fruit shape and flesh characteristic when fully tree ripe. The fruit is further characterized by having good balance between sugar and acid, with a high degree of soluble solids (average 15 Brix), which is higher than most commercially grown apricots in California.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to reveal flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Usually pruned to vase shape.
- *Productivity.*—Productive.
- *Bearer.*—Regular.
- *Density.*—Medium.
- *Growth.*—Semi-spreading.

Trunk:
- *Size.*—Large.
- *Texture.*—Shaggy.
- *Color.*—Brown to dark brown (6-E-7) to (6-F-8).

Branches:
- *Size.*—Medium to large.
- *Texture.*—Smooth to medium rough. Varies with age of growth.
- *Lenticels.*—Numerous. Small in size.
- *Color.*—Light brown to brown (5-D-5) to (5-E-4), varies with age of growth.

Leaves:
- *Size.*—Medium to large. Average length 4⅛". Average width 2⅝".
- *Form.*—Ovate, pointed.
- *Margin.*—Serrate.
- *Thickness.*—Medium.
- *Surface.*—Smooth.
- *Petiole.*—Medium length (average 1⅜"). Medium thickness.
- *Glands.*—Number varies from 1 to 3. Average number 2. Small size. Globose. Located on upper portion of petiole and base of leaf blade.

*Color.*—Upper surface — light green to green (29-F-6) to (29-F-8). Lower surface — dull green to grayish green (29-D-7) to (29-D-8).

Flower buds:

*Size.*—Medium to large.

*Length.*—Medium.

*Form.*—Plump.

Flowers:

*Size.*—Large.

*Pollen.*—Present.

*Blooming period.*—Date of first bloom: Feb. 12, 1996. Date of last bloom: Feb. 18, 1996. Varies slightly with climatic conditions.

*Color.*—Light pink, fades to white at petal fall.

Fruit:

*Maturity when described.*—Firm ripe.

*Date of first picking.*—May 20, 1996.

*Date of last picking.*—May 24, 1996. Varies slightly with climatic conditions.

*Size.*—Medium. Average diameter axially 2⅜". Average transversely in suture plane 2". Average diameter measured at right angles to suture plane 1⅞".

*Form.*—Elongated, each side slightly compressed inwardly toward the suture.

*Suture.*—Extends from base to apex.

*Ventral surface.*—Slightly lipped, varies from slightly lipped to round.

*Apex.*—Nearly rounded.

*Base.*—Retuse.

*Cavity.*—Rounded to slightly elongated in suture plane. Average depth ¼". Average breadth ½".

Flesh:

*Ripens.*—Evenly.

*Texture.*—Firm, meaty.

*Fibers.*—Few, very small, tender.

*Aroma.*—Slight.

*Eating quality.*—Very good.

*Flavor.*—Very good.

*Color.*—Orange to persian orange (6-A-7) to 6-B-8). Pit cavity only slightly darker orange (6-C-8).

Skin:

*Thickness.*—Medium.

*Texture.*—Medium, tenacious to the flesh.

*Down.*—Moderate, very short.

*Tendency to crack.*—None.

*Color.*—Orange to dark orange. (7-B-7) to (7-C-8).

Stone:

*Type.*—Freestone.

*Size.*—Medium. Average length 1¼". Average width ⅞". Average thickness ½".

*Form.*—Ovoid.

*Base.*—Mostly straight, varies from straight to rounded.

*Apex.*—Usually rounded, slight tip on some stones.

*Surface.*—Very lightly pitted throughout. Small narrow ridges running toward apex. Usually two distinct ridges across surfaces of stone on both sides of suture.

*Sides.*—Unequal.

*Tendency to split.*—None.

*Color.*—Light brown to brown (5-D-5) to (5-E-6).

Use: Dessert. Maket, local and long distance.

Keeping quality: Good.

Shipping quality: Good.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct interspecific tree, substantially as illustrated and described, characterized by its large size, vigorous, semi-spreading growth and a productive, regular bearer of medium size, orange flesh, freestone fruit with very good flavor and eating quality; the fruit is further characterized by having firm flesh with a high degree of soluble solids (average 15 Brix), having good handling and shipping quality, and having a high degree of attractive orange skin color.

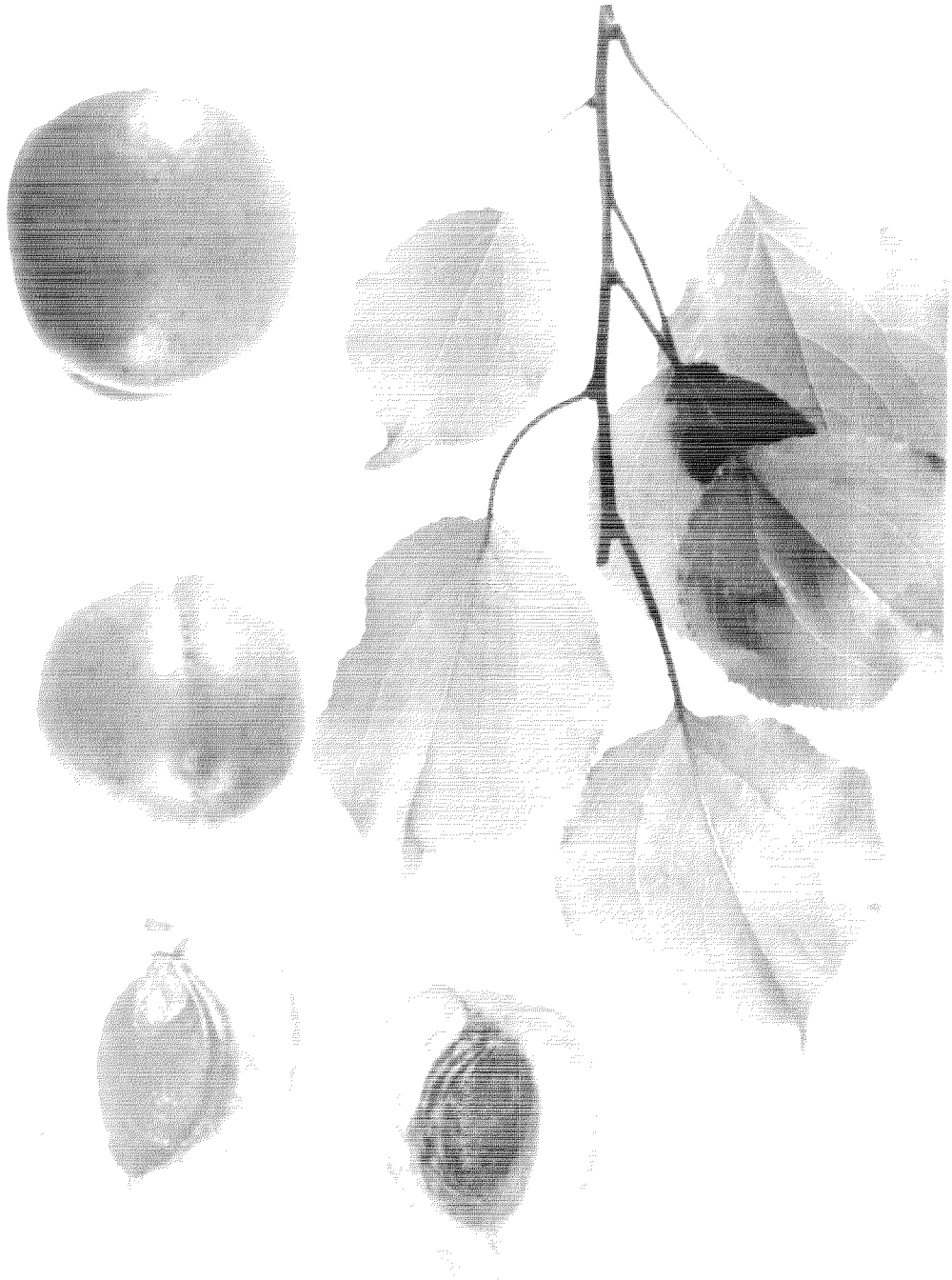

* * * * *